(12) United States Patent
Hu et al.

(10) Patent No.: US 7,347,988 B2
(45) Date of Patent: Mar. 25, 2008

(54) SYNTHESIS, USES AND COMPOSITIONS OF CRYSTAL HYDROGELS

(75) Inventors: Zhibing Hu, Denton, TX (US); Xihua Lu, Denton, TX (US); Jun Gao, Burnaby (CA); Tong Cai, Denton, TX (US); Gang Huang, Denton, TX (US); Bo Zhou, Denton, TX (US)

(73) Assignee: University of North Texas, Denton, TX (US)

( * ) Notice: Subject to any disclaimer, the term of this patent is extended or adjusted under 35 U.S.C. 154(b) by 551 days.

(21) Appl. No.: 10/295,484

(22) Filed: Nov. 15, 2002

(65) Prior Publication Data

US 2004/0018160 A1   Jan. 29, 2004

Related U.S. Application Data

(60) Provisional application No. 60/336,259, filed on Nov. 15, 2001.

(51) Int. Cl.
   *A61K 7/021* (2006.01)

(52) U.S. Cl. .................. 424/63; 424/486; 424/488; 524/563; 525/88

(58) Field of Classification Search .............. 424/63, 424/486, 488; 525/88; 524/563
   See application file for complete search history.

(56) References Cited

U.S. PATENT DOCUMENTS

| | | | |
|---|---|---|---|
| 4,555,344 | A | 11/1985 | Cussler |
| 4,732,930 | A | 3/1988 | Tanaka et al. |
| 4,912,032 | A | 3/1990 | Hoffman et al. |
| 5,062,841 | A | 11/1991 | Siegel |
| 5,100,933 | A | 3/1992 | Tanaka et al. |
| 5,183,879 | A | 2/1993 | Yuasa et al. |
| 5,403,893 | A | 4/1995 | Tanaka et al. |
| RE35,068 | E | 10/1995 | Tanaka et al. |

(Continued)

FOREIGN PATENT DOCUMENTS

EP            636635 A2 *  2/1995

OTHER PUBLICATIONS

Hirotsu, et al., "Volume-phase transitions of ionized N-isopropylacrylamide gels," J. Chem. Phys. 87, 1392-95 (1987).

(Continued)

*Primary Examiner*—David W. Wu
*Assistant Examiner*—Henry S. Hu
(74) *Attorney, Agent, or Firm*—Jackson Walker L.L.P.

(57) ABSTRACT

A method is disclosed for creating hydrogels with ordered crystalline structures that exhibit a characteristic colored opalescence. In addition to the unique optical properties, these materials contain a large amount of water in their crosslinked networks. The manufacturing processes include synthesizing monodispersed hydrogel nanoparticles containing specific reactive functional groups, self-assembly of these particles to form a crystalline structure, and subsequent crosslinking neighboring spheres to stabilize the entire network. Polymerizing a hydrogel monomeric composition around the crystalline structure can enhance the mechanical strength. The resulting network is dimensionally and thermodynamically stabile under various pH and temperature conditions. The color and volume of these crystalline hydrogel networks can reversibly change in response to external stimuli such as temperature, pH and other environmental conditions. These new materials may lead to a variety of technological and artistic applications, ranging from sensors, displays, controlled drug delivery devices, jewelry and decorative consumer products.

27 Claims, 13 Drawing Sheets

U.S. PATENT DOCUMENTS

| | | | |
|---|---|---|---|
| 5,532,006 | A | 7/1996 | Lauterber et al. |
| 5,580,929 | A | 12/1996 | Tanaka et al. |
| 5,654,006 | A | 8/1997 | Fernandez et al. |
| 5,976,648 | A | 11/1999 | Li et al. |
| 6,014,246 | A | 1/2000 | Asher et al. |
| 6,030,442 | A | 2/2000 | Kabra et al. |
| 6,165,389 | A | 12/2000 | Asher et al. |
| 6,187,599 | B1 | 2/2001 | Asher et al. |
| 6,194,073 | B1 | 2/2001 | Li et al. |
| 6,350,812 | B1 * | 2/2002 | Vert et al. .................... 524/845 |
| 6,521,431 | B1 * | 2/2003 | Kiser et al. ................. 435/177 |
| 6,946,086 | B2 * | 9/2005 | Foulger et al. ............. 252/586 |

OTHER PUBLICATIONS

Hu, et al., "Hydrogel Opals," Adv. Mater. 13, 1708-12 (2001).

Hu, et al., "A New Route to Crystalline Hydrogels, Guided by a Phase Diagram," Angew. Chem. Int. Ed. 42, 4799-802 (2003).

Hu, et al., "Polymer Gel Nanoparticle Networks," Adv. Mater. 12, 1173-76 (2000).

Hu, et al., "Synthesis and Application of Modulated Polymer Gels," Science 269, 525-27 (1995).

Chen, et al., "Graft copolymers that exhibit temperature-induced phase transitions over a wide range of pH," Nature 373, 49-52 (1995).

Pusey, et al., "Phase behavior of concentrated suspensions of nearly hard colloidal spheres," Nature 320, 340-42 (1986).

Senff, et al., "Temperature sensitive microgel suspensions . . . " J. Chem. Phys. 111, 1705-11 (1999).

Siegel, et al., "pH-Dependent Equilibrium Swelling Properties of Hydrophobic Polyelectrolyte Copolymer Gels," Macromol. 21, 3254-59 (1988).

Osada, et al., "Intelligent Gels," Scie. Ame. 268, 82-87 (1993).

Tanaka, "Collapse of Gels and the Critical Endpoint," Phys. Rev. Lett. 40, 820-23 (1978).

Weissman, "Thermally Switchable Periodicities and Diffraction from Mesoscopically Ordered Materials," Science 274, 959-60 (1996).

* cited by examiner $R_h = 237$ nm  $R_h = 248$ nm 0M  0.1M  0.5M  1.2M

SYNTHESIS, USES AND COMPOSITIONS OF CRYSTAL HYDROGELS

Priority is claimed from provisional patent application number Ser. No. 60/336,259, filed on Nov. 15, 2001.

FIELD OF THE INVENTION

The present invention relates to the fields of polymer chemistry and material science. In particular, it relates to the process of producing monodispersed, hydrogel nanoparticles and subsequent self-assembly and crosslinking, providing materials that are crystalline in structure displaying characteristic opalescence.

BACKGROUND OF THE INVENTION

Gels are three-dimensional macromolecular networks that contain a large fraction of solvent within their structure and do not dissolve. When the trapped solvent is water, the gels are termed "hydrogels". Hydrogels exhibit high water content and are soft and pliable. These properties are similar to natural tissue, and therefore hydrogels are extremely biocompatible and are particularly useful in biomedical and pharmaceutical applications.

Hydrogels can be responsive to a variety of external, environmental conditions. A unique physical property of some hydrogel systems is reversible volume changes with varying pH and temperature. This unique property and other characteristics are thoroughly detailed in the scientific reference articles cited above.

Some diversified uses of responsive gels include solute/solvent separations, biomedical tissue applications, controlled drug delivery, sensors and devices, and in NMR contrast agents. These applications are disclosed in U.S. Pat. Nos. 4,555,344, 4,912,032, 5,062,841, 5,976,648 and 5,532,006, respectively.

Polymer gels can be formed by the free radical polymerization of monomers in the presence of a reactive crosslinking agent and a solvent. They can be made either in bulk or in nano- or micro-particle form. The bulk gels are easy to handle, but usually have very slow swelling rates and amorphous structures arising from randomly crosslinked polymer chains. In contrast, gel nanoparticles react quickly to an external stimulus, have organized local structure, but suffer from practical size limitations.

Responsive polymer gels can be made by the co-polymerization of two different monomers, by producing interpenetrating polymer networks or by creating networks with microporous structures. These processes are disclosed in U.S. Pat. Nos. 4,732,930, 5,403,893, and 6,030,442, respectively. Finally, a microparticle composition and its method of use in drug delivery and diagnostic applications have also been disclosed in U.S. Pat. No. 5,654,006.

Hydrogels usually consist of randomly crosslinked polymer chains and contain a large amount of water occupying interstitial spaces of the network, resulting in amorphous structures. Without the addition of a coloring agent or opacifier, hydrogels are clear and colorless when they are fully swollen in water. To create colors in hydrogel systems, there are two major approaches in the prior art as disclosed in U.S. Pat. Nos. 6,165,389, 6,014,246 and 6,187,599. The first is to form a poly(N-isopropylacrylamide) (P-NIPA) crystalline colloidal fluid in an aqueous media and contain it in a glass cell. The second is to embed a crystalline colloidal array of polystyrene polymer solid spheres in a P-NIPA hydrogel. Both approaches have utilized the unique temperature-responsive property of the P-NIPA, but each has its own limitations. The first material is a colloidal fluid: its crystal structure can be easily destroyed by a small mechanical vibration. The second approach to make colored hydrogels requires the introduction of non-hydrogel solid spheres (polystyrene) as light-diffracting materials.

The concept for synthesizing crystal hydrogels based on crosslinking gel nanoparticles was first alluded to in provisional patent application Ser. No. 60/336,259. The nanoparticle networks as described in that patent application exhibit either a uniform color due to a short-range ordered structure or are colorless due to a randomly ordered structure.

The primary scope of this invention relates to environmentally responsive hydrogel nanoparticle networks that exhibit crystalline structures, are opalescent in appearance, are stable under mechanical vibration and temperature fluctuations, and consist of only hydrogel materials without other embedded solid polymer spheres.

SUMMARY OF THE INVENTION

The main objective of this invention is to provide a composition and process to create hydrogel nanoparticle crystalline networks that have a long-range ordered structure. Another objective is to produce crystal networks that are dimensionally stable under mechanical vibration and temperature fluctuation, display a unique color and sparkle when viewed at different angles and under different lighting, and consist of only mondispersed hydrogel nanoparticles without embedded solid polymer spheres of a different composition. A further objective is to produce hydrogel crystal networks in the absence of any organic solvents. These objectives have been accomplished by producing monodispersed, temperature responsive nanoparticles in water, self-assembly of these nano-spheres, subsequent crosslinking of nanoparticle spheres through covalent bonding and polymerizing a hydrogel monomeric composition around the crystalline structure to enhance the mechanical strength. The nanoparticle self-assembly provides the hydrogels with crystal structures while the covalent bonding and secondary hydrogel encasing contributes to the mechanical, dimensional, and thermal stability of these materials. These networks diffract light, resulting in a rich array of speckled colors. Furthermore, the crystal hydrogels in water display an iridescent color with good transparency and no sedimentation (without adding an index-matching or a density-matching fluid).

This invention disclosure will also teach a process for crosslinking nanoparticles in aqueous media that is unique in its application to hydrogels. The covalent linkages between nanoparticles lead to an unexpected thermal and dimensional stability of the resulting crystal structure. For example, the colored refraction from crystalline facets at room temperature disappear when a sample was heated to 50° C., at which point the gel network became cloudy due to phase separation. When the sample was cooled back to 21° C., the pattern reappeared within 10 seconds. The process was reversible through multiple iterations. In contrast, a non-crosslinked nanoparticle assembly of the same composition and concentration was completely disrupted as the temperature was raised to 32° C. It required approximately 1000 times longer for a non-crosslinked assembly to re-assemble into a crystal structure.

The most important commercial property of these materials is the inherent presence of a long-range crystalline order. A crystalline lattice allows for the formation of one large bulk gel in which any smaller piece of the material has the exact same physical properties as the bulk material. This is a property previously found only in hard materials such as metals, semiconductors or opals. Applying crystallinity to a soft material with environmental responsiveness provides a stable material with potential applications not previously available to hydrogel polymer or gel-based systems. This allows the production of hydrogel-based systems incorporating their many useful properties while giving absolute control over the entire structure down to the nanometer scale.

One consumer application of these new materials described above could be a decorative home product or toy: the hydrogel nanoparticle water dispersion would be pre-injected into a glass or plastic container of any desired shape. Then, by adjusting temperature and/or pH of dispersion, the nanoparticles can self assemble into poly-crystals with rich opalescent colors due to multiple light diffraction patterns resulting from these crystals. Then, the assembly would be dimensionally stabilized by subsequent crosslinking of the nanoparticles via heat and/or light. The complete process will be safe, innocuous, and potentially inexpensive since the majority of the product is essentially water.

Another potential consumer product could be exotic opalescent jewelry. These crosslinked, hydrogel nanoparticle water networks could be encased inside a plastic, transparent shape retentive and formative material. Upon viewing these networks at different angles and under various lighting conditions, multiple light diffraction patterns occur similar to those observed when viewing a prism. A wide range of colors and sparking effects result, enhancing the visual appearance as required and inherent to expensive diamonds or other precious gems used in jewelry.

The environmental responsiveness of the crystalline nanoparticle networks, coupled with their inherent stability and reversibility gives rise to sensor applications. As the nanoparticle environment changes, the optical properties of the material show a corresponding effect. This allows potential in-situ monitoring of changes in temperature, or chemical environment. Coupling this with the biological inertness of the material allows for the formation of in-vivo sensors. Incorporation of chemically degradable crosslinkers in the network could allow for the formation of specific chemical sensors detecting changes in pH or the presence of specific enzymes.

One pharmaceutical application relates to the controlled delivery of active compounds for the treatment of a variety of diseases. A drug can be entrapped inside the crystal network during the crosslinking step that dimensionally stabilizes the network. By regulating the crosslinking density and type, multiple ordered lattices can be produced. Crystalline lattices contain ordered voids depending on the type of lattice formed. These "holes" in the networks would allow different molecular weight actives based on size to elute out at a controlled rate. One can also envision using biodegradable crosslinkers, so as they degrade, the network will break apart, releasing the active, entrapped compound. One important reason to use these materials for controlled drug delivery is the presence of opalescence. This property provides a direct visual indication that the networks are uniform, homogeneous and have been manufactured appropriately. Simple turbidity techniques can be used to detect non-homogeneity in the crystal lattice, providing feedback on sample quality and uniformity.

DETAILED DESCRIPTION OF THE PREFERRED EMBODIMENTS

Figure 1:
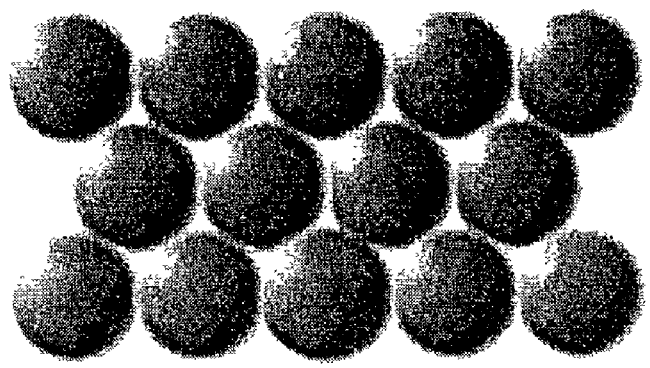
FIG. 1 is a schematic illustration of a crystal hydrogel that consists of a crystal assembly of covalently bonded monodispersed hydrogel nano-spheres.

A conceptual model is shown in FIG. 1. The manufacturing methods consists of three steps: (1) synthesis of monodispersed polymer gel nanoparticles having specific reactive groups suitable for crosslinking, (2) self-assembly of the nanoparticles into a crystal structure, and (3) covalent bonding of the network to form a stable lattice. Additionally, polymerizing a hydrogel monomeric composition around the crystalline structure can enhance the mechanical strength if needed. The covalent bonding contributes to the structural stability, while self-assembly provides large crystal grain structures, resulting in refractive colored facets throughout the network in addition to light scattering properties exhibited by natural crystals.

Figure 2:
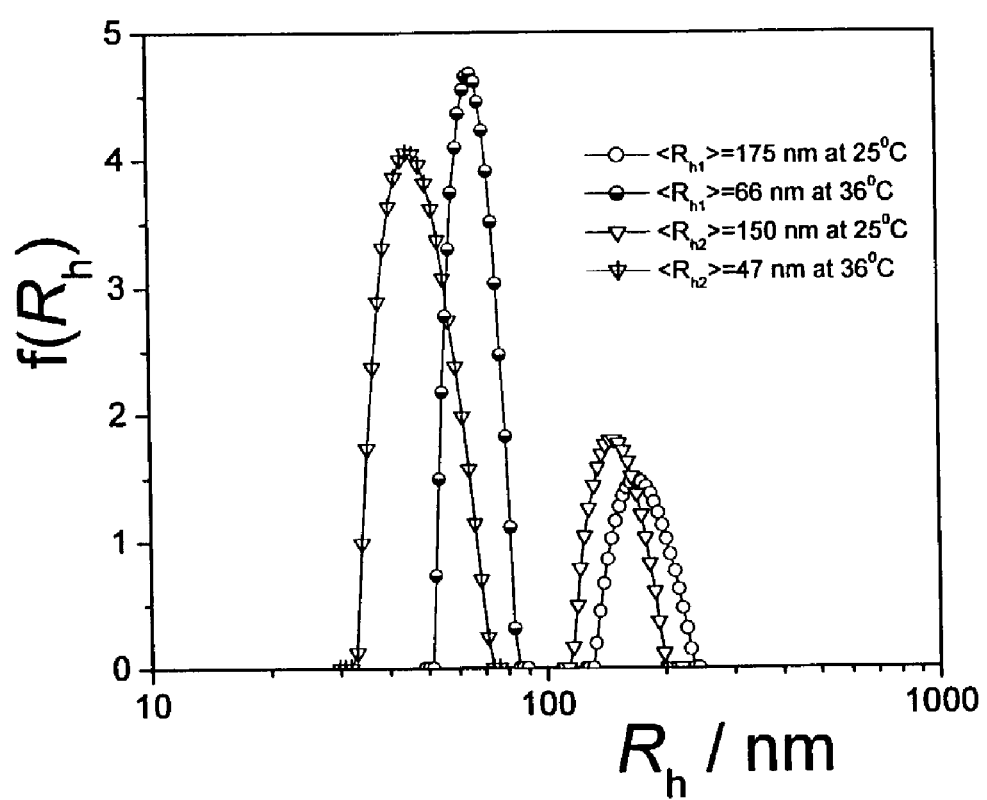
FIG. 2 is a graph depicting hydrodynamic radius distributions ($f(R_h)$) of NIPA-HEAc nano-spheres synthesized under different surfactant concentrations (see Table 1) in water at T=25.0° C. and 36.0° C., respectively. Here the polymer weight percent $C=1.37 \times 10^{-5}$ g/g, and the scattering angle is 20°.

Monodispersed hydrogel nanoparticles can be prepared by an emulsion method. Preferred major monomer is N-isopropylacrylaimde (NIPA) or other related analogs. Preferred co-monomers are hydroxyethyl acrylate (HEAc), allylamine, acrylic acid, and other related analogs. For example, co-polymer nanoparticles composed of 90% NIPA and 10% 2-hydroxyethyl acrylate using an emulsion polymerization method were produced. The size distribution of nanoparticles was characterized using a light scattering spectrometer (ALV-5000). The hydrodynamic radius of the resultant nanoparticles in water was narrowly distributed with a size variance of about 1% as shown in FIG. 2. The NIPA has a thermally responsive property, while the HEAc provides hydroxyl (—OH) groups for subsequent crosslinking.

Figure 3:
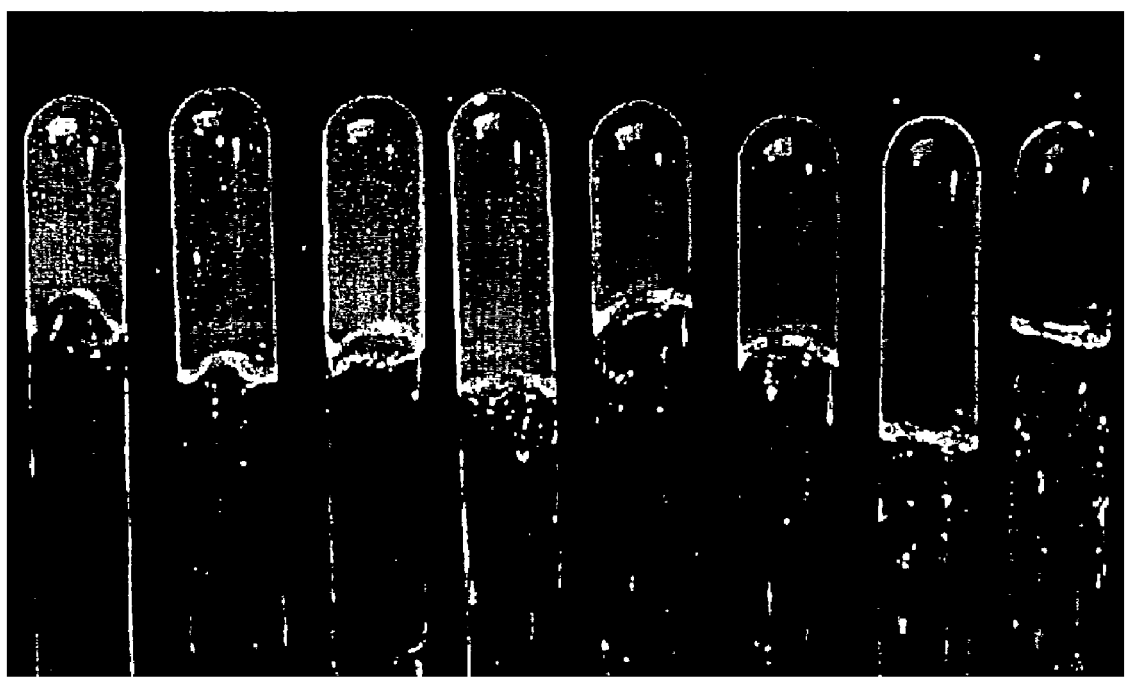
FIG. 3 shows the optical property of the NIPA-HEAc colloidal crystals. The turbidity is plotted as a function of wavelength for two NIPA-HEAc colloidal crystals in water at room temperature. The peak indicates crystal structure. The nanoparticles of two hydrogels in water at 25° C. had an average hydrodynamic radius of 150 nm and 160 nm, respectively.

The NIPA-HEAc nanoparticle water dispersion was condensed to a desired concentration by either ultra-centrifuging or evaporating method. At a suitable polymer concentration, nanoparticles form a crystalline structure. To quantify this observation, the turbidity of the NIPA-HEAc colloidal crystal as a function of light wavelength was measured as shown in FIG. 3 using a spectrophotometer. Corresponding to the appearance of colored speckles, the turbidity of the colloidal crystal exhibited a peak at a specific wavelength, $\lambda_c$. $\lambda_c$ is proportional to the periodicity of the crystal. The colored speckles of the samples arise directly from selective Bragg diffraction at $\lambda_c$. Specifically, the Bragg condition of $2n \sin \theta = m\lambda_c$ is satisfied with the diffraction angle $\theta=90°$ and $m=1$. Here n is the refractive index of the hydrogel nanoparticles. Because the periodicity can be adjusted by varying either the concentration or the particle size, the colors of the samples can be shifted accordingly.

The crystalline structure was then stabilized by linking nanoparticles together using a small molecular crosslinker. Preferred crosslinking agents include divinylsulfone (DVS), glutaric dialdehyde, a mixture of 1-ethyl-3-(3-dimethylaminopropyl) carbodiimide hydrochloride (EDC) and adipic acid dihydrozide, and epichlorohydrin (EPO). For example, after the self-assembling occurred, divinylsulfone was added to bond the NIPA-HEAc nanoparticles at room temperature. The more crosslinking agent used the higher the rigidity and the lower the pore size of the resulting crystal hydrogels. Thus, one can choose an appropriate amount and type of crosslinker to provide the mechanical strength and porosity desired for a variety of diversified applications. Since this crosslinking process is carried out directly in water, it is particularly useful for hydrogels. Furthermore, because the colloidal particles are linked together by covalent bonding, they cannot be re-dispersed into a solution, in contrast to well-known colloidal aggregates described in the prior art.

Figure 4:
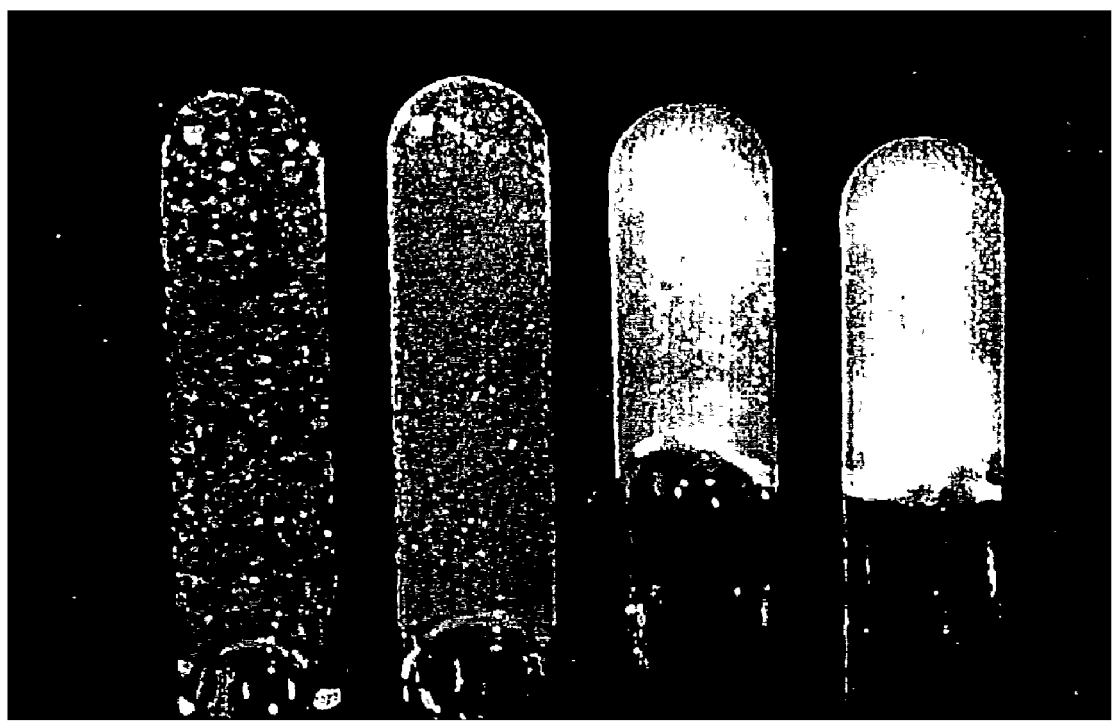
FIG. 4 shows photographs of the covalently bonded, self-assembled NIPA-HEAc nanoparticles at various particle concentrations. From left to right: 3.5, 3.8, 3.9, 4.1, 5.0, 5.5, 6.0, and 7.9 wt %. Here, the average hydrodynamic radius of the NIPA nanoparticle spheres in water at 25° C. was 150 nm.

The resultant NIPA-HEAc crystal hydrogels are shown in FIG. 4. In contrast to other colloidal fluids known in the art, these hydrogels are solids and thus do not significantly deform due to gravity. This is apparent by viewing these networks when their formation tubes are inverted.

It is obvious by one skilled in the art, other suitable monomers with functional groups, crosslinkers, surfactants and initiators can be used, absent of compatibility problems.

Formation of a crystal hydrogel depends strongly on the polymer concentration in the pre-gel nanoparticle solution. In general, below 1 wt %, the particles are too far apart and could not be easily bonded together. Conversely, when the concentration is above 10 wt %, the nanoparticles are too close to each other and then lose the mobility that is required to form crystals. There are many factors that can make this polymer concentration vary between 1 to 10 wt % become narrower including particle size, functional groups on the particle surface, reaction temperature, pH values, quality of solvent (water or organic solvent), condensation methods (evaporation or ultracentrifugation), etc. Below the polymer concentration range for the crystal formation, the nanoparticles are in a fluid state. Above this range, the bonded nanoparticles exhibit a uniform color with no iridescence and the methods of manufacture have been disclosed in the aforementioned provisional patent application.

Figure 5:
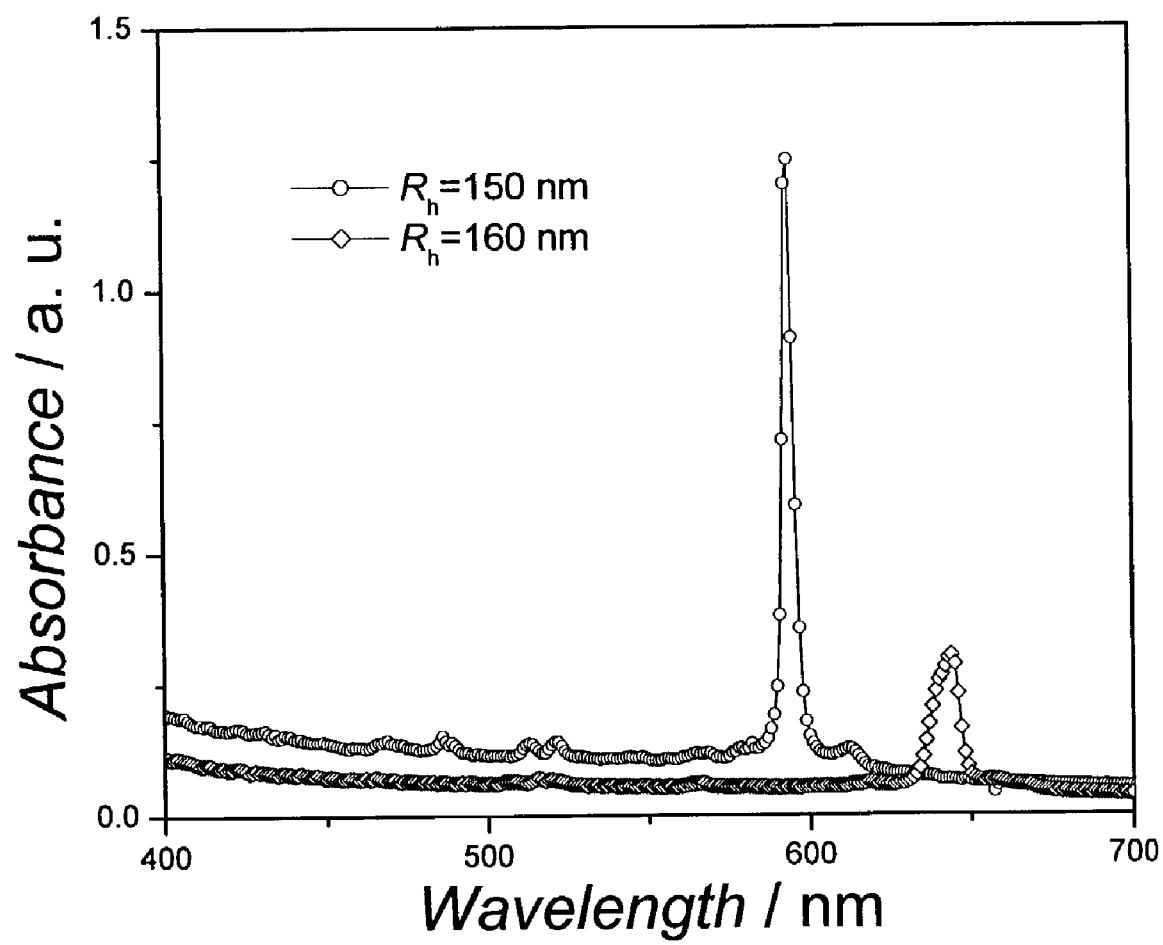
FIG. 5 shows the effect of NIPA-HEAc particle size on the formation of crystal hydrogels. The average hydrodynamic radii for the two red samples (left) and the two green samples (right) in water at room temperature were 175 and 150 nm, respectively. From left to right, the particle concentrations were 3.0, 3.1, 3.8, and 4.0 wt %.

For example, this invention relates to the formation of crystal hydrogels using a very narrowly distributed, monodispersed NIPA-HEAc nanoparticles as building blocks. These crystal hydrogels unexpectedly exhibit a striking colored speckled array due to light diffraction by large-sized crystal domains. The crystal grain size also decreases with increasing concentration within this concentration range from 2.9 to 5 wt %. Also, as the particle size increases, the color shifted to the red region and the crystal phase occurred at a lower concentration as shown in FIG. 5.

The crosslinked crystal hydrogel networks have good mechanical strength relative to other colloidal crystals that are fluids and have a zero static shear modulus. The NIPA-HEAc crystal hydrogel was taken out of a glass tube and immersed in a pH=2.5 solution at room temperature as shown in the top panel of FIG. 6. The colored speckles of the sample are a clear indication that the sample has retained the crystal structure of its colloidal precursor. After applying a weight (a transparent dish) on the sample's upper surface, the sample was compressed (the bottom panel, FIG. 6) and greatly deformed. The fractional increase in length was 80% along the radial direction and 40% along the longitudinal direction. Once the weight was removed, however, the network immediately returned to its original shape due to its elasticity and re-exhibited the iridescent pattern, as shown in the top panel. It is also noted that colored speckles are usually associated with rigid materials such as precious opals that can deform slightly, or with colloidal fluids that have no definite shape. Here, a soft material that is elastic, wet, and exhibiting an iridescent pattern has been created.

Figure 7:
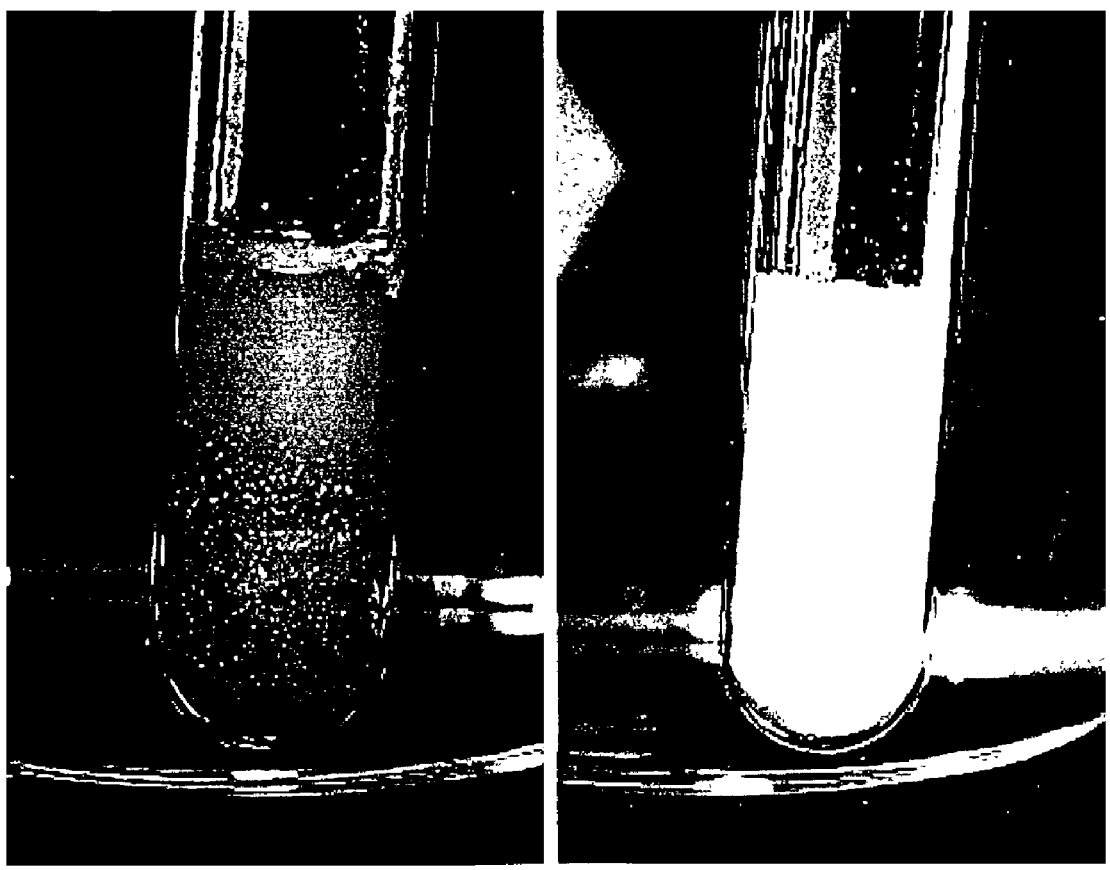
FIG. 7 shows a display based on crystal hydrogels. A NIPA-HEAc crystal hydrogel in a glass tube is transparent and exhibited a colored, speckled iridescent pattern at 21° C. (left) until the temperature was raised to 50° C. (right), at which point the pattern became invisible. As the sample at 50° C. was cooled back to 21° C., the patterns reappeared within 10 seconds.

The covalent linkages between nanoparticles also lead to a remarkable thermal stability of the crystal structure. FIG. 7 shows the temperature dependence of a crystal hydrogel in a tube after polymerization. The iridescent pattern (left panel) at room temperature became invisible when the sample was heated to 50° C., at which point the gel became cloudy due to phase separation (right panel). When the sample at 50° C. was cooled back to 21° C., the pattern reappeared within 10 seconds, and this process was reversible. In contrast, a non-crosslinked nanoparticle assembly with the same concentration was completely disrupted as the temperature was raised to 30° C. It required about 1000 times longer for a non-crosslinked assembly to re-assemble into a crystal structure. It is apparent that disturbed nanoparticles in a crosslinked assembly are able to return to their equilibrium crystalline positions quickly through restorative forces provided by the network's elasticity. The fast and reversible response rate of these crystal hydrogels could be a major advantage in developing sensor or display technologies as compared to using conventional colloidal crystal arrays known in the art.

It is noted from the left panel in FIG. 7 that the crystal hydrogel in water displays an iridescent color with good transparency and no sedimentation (without adding an index-matching or a density-matching fluid). This is because the building blocks are hydrogel nanoparticles which contain up to 97 wt % water; both the refractive index and the density of the particles are nearly matched with those of the surrounding water. The crystal structures of these systems are further enriched by their unique two-level structural hierarchy: the primary network consists of crosslinked polymer chains inside each nanoparticle, while the secondary network is a crosslinked system of the nanoparticles. The mesh sizes of the primary and the secondary networks are usually around 1-10 nm and 10-500 nm respectively.

There are a variety of crosslinkers that can be used to bond nanoparticles into a crystal hydrogel including divinylsulfone (DVS), glutaric dialdehyde, a mixture of 1-ethyl-3-(3-dimethylaminopropyl)carbodiimide hydrochloride (EDC) and adipic acid dihydrozide, and epichlorohydrin (EPO).

To use glutaric dialdehyde as a crosslinker, NIPA-co-allylamine nanoparticles were first synthesized using an emulsion polymerization. Allylamine offers the free amine function groups on the surface of the particles for further crosslinking. The hydrodynamic radius of the nanoparticles in water was narrowly distributed. The average hydrodynamic radius at 23° C. is about 140 nm. After using ultra centrifuge with the speed of 40,000 rpm for 2 hrs, we obtained condensed particle dispersions with solid content between 3 and 4%. Then, 25 wt % glutaric dialdehyde was added and mixed into the solution. The crosslinking reaction was carried out at room temperature for 24 hours, resulting in a bright iridescent crystal hydrogel.

Figure 8A:
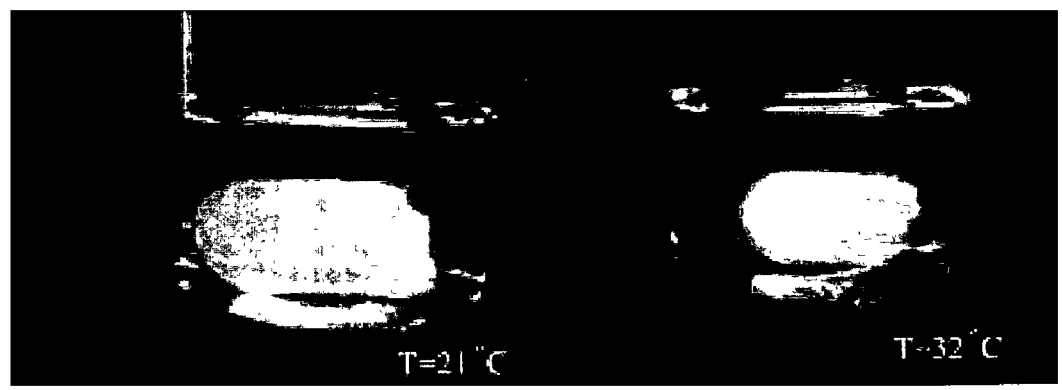
FIG. 8. Environmental responsive behavior of the crystal hydrogel that consists of covalently bonded, self-assembled NIPA-co-allylamine nanoparticles. The average hydrodynamic radius for the particles in water at 23° C. is 140 nm. (a) Temperature dependence: from left to right, top to bottom: 21, 32, 34 and 35° C., respectively; (b) pH dependence: from let to right, pH=6.5 and pH=11.
Figure 8A:
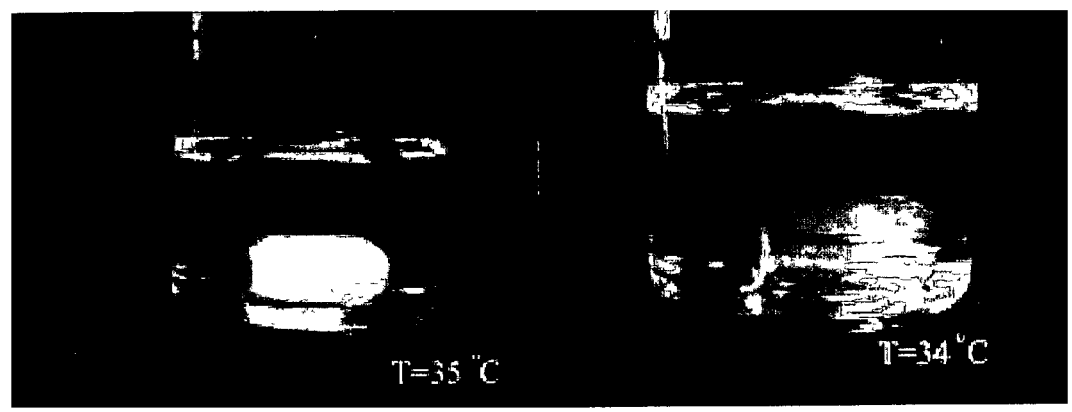
Figure 8B:
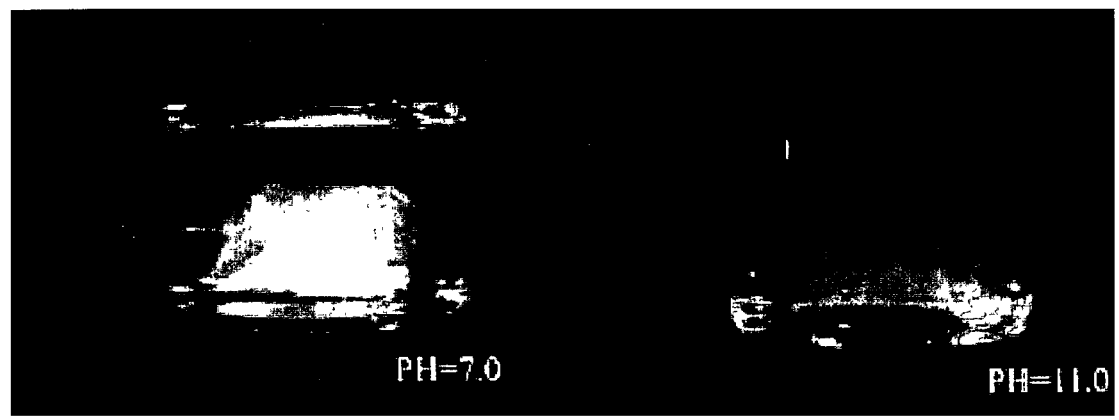

Because the crystal hydrogel composed of poly(NIPA-co-allylamine) nanoparticles arranged in a close-packed structure, the lattice spacing between particles will undergo a change in responsive to environmental stimuli. FIG. 8a shows that the color and volume changes of the crystal hydrogel as a function of temperature. As the temperature increases, the volume of the gel decreases and its color shifts from green to blue and eventually to milky white when the temperature is above the volume phase transition temperature about 34° C. FIG. 8b shows the pH dependent volume and color change of the NIPA-co-allylamine crystal hydrogel. This is caused by the different degrees of ionization of amine groups on the polymer chains at different pH values.

To use a mixture of 1-ethyl-3-(3-dimethylaminopropyl) carbodiimide hydrochloride (EDC) and adipic acid dihydrozide as a crosslinker, poly(NIPA-co-acrylic acid) (NIPA-co-AA) nanoparticles were first synthesized using emulsion polymerization. Acrylic acid offers —COOH groups on the surface of the particles for further crosslinking.

Figure 9:
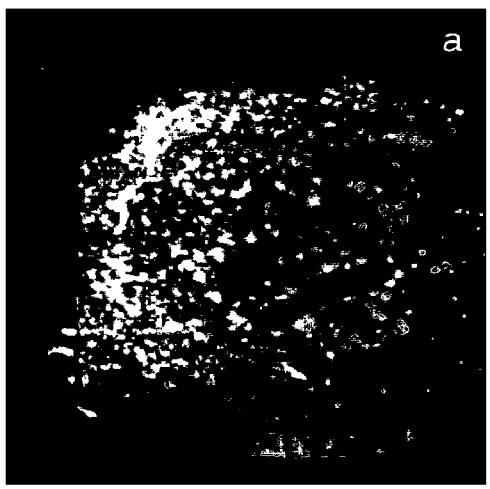
FIG. 9 shows the crystal hydrogels that consists of covalently bonded, self-assembled NIPA-co-acrylic acid nanoparticles with different hydrodynamic radii at room temperature in water: (a) $R_h$=237 nm and (b) $R_h$=248 nm.
Figure 9:
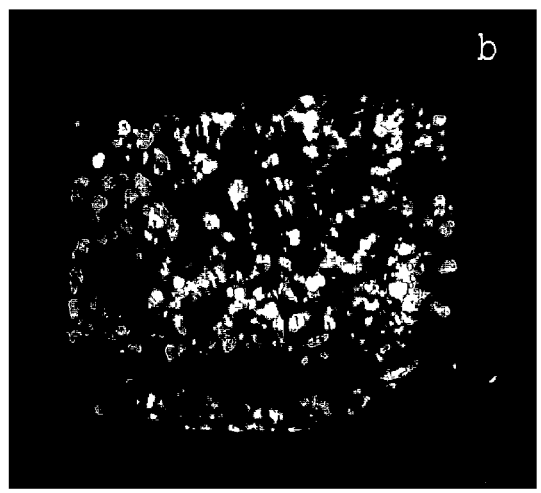

The NIPA-co-AA nanoparticles (210 nm) were then concentrated below 50° C. for two days. The NIPA-co-AA nanoparticle water dispersion at a solid content of 3.1 wt % was put into a special cylindrical tube with a large amount of holes (0.5 mm in diameter) in the wall and the bottom. The NIPA-co-AA particles self-assemble into a crystalline array within 5 h. Then, the tube was half-immersed into 1-ethyl-3-(3-dimethylaminopropyl) carbodiimide hydrochloride (EDC or EDAC) (5 wt %) and adipic acid dihydrazide (AADD) (5 wt %). This assembly was kept at 4° C. for 24 hours and then 5% EDC and AADD solution was replaced with a fresh 7 wt % EDC and 7 wt % AADD solution. After another 24 hours, the NIPA-co-AA nanoparticles were covalently bonded into a crystalline hydrogel as shown in FIG. 9.

To use epichlorohydrin (EPO) as a crosslinker, poly (NIPA-co-AA) nanoparticles were synthesized using emulsion polymerization. These particles were cooled down to room temperature and precipitated with acetone. The precipitated particles were dried for 2 days and then re-suspended in acetone. The Poly-NIPAAm-co-AA particles self-assemble into a crystalline structure at 10 wt % concentration at room temperature. Then, epichlorohydrin (EPO) (10 wt. %) was added into the solution. The crosslinking reaction was conducted in the oven at 90° C. for 6 hours. The resultant crystal gel was then taken out from the tube and immersed into acetone. Acetone was then gradually replaced with water to obtain a crystalline hydrogel.

The crystal hydrogels can be strengthened by filling the pores between nanoparticles with a secondary hydrogel matrix. This is a two-step process including: (1) covalently bonding neighboring nanoparticles to stabilize the periodic structure, and (2) polymerizing the secondary matrix around nanoparticles. Here, the covalent bonding between particles contributes to stabilizing periodic structure, while the formation of the hydrogel matrix around each particle contributes to enhancing mechanical strength. Without the first step, polymerization of the secondary hydrogel matrix can completely disrupt the periodic stacking of the particles.

To obtain this high strength crystal hydrogel, NIPA-HEAc nanoparticles were first made following the method described above. This NIPA-HEAc nanoparticle dispersion was then diluted with monomer solution that contained NIPA monomer, sodium acrylate as ionic group, photosensitive initiator of 2,2-diethoxyacetophenone, and N,N'-methylenebisacrylamide as a crosslinker. The polymer concentration of the particles was 2.0 wt %, while the monomer concentration was in the range between 2.5 to 6 wt % in the final dispersion. The dispersion was thoroughly bubbled with nitrogen gas to remove oxygen. This dispersion was heated to 40° C., at which point divinylsulfone (DVS) as a crosslinking agent was added to the system. Then, the dispersion was cooled below 25° C., and NaOH solution was added to adjust the pH to 13. The formation of colloidal crystals yielded colored speckles as a result of typical Bragg diffraction. After observing the iridescence from the sample, the nanoparticles were crosslinked to stabilize the crystal structure for 24 hours. The polymerization of the secondary hdyrogel matrix was carried out using a UV lamp to initiate polymerization of the NIPA and sodium acrylate monomers. The sample was kept in the nitrogen environment for 24 hr for completing gelation. This resulting crystal hydrogel consists of periodically stacked NIPA-HEAC nanoparticles for Bragg diffraction encased in the NIPA-co-sodium acylate polymer for enhancing materials strength and providing other environmentally responsive properties to the crystalline hydrogel.

The shear modulus of the crystal hydrogel encased within a secondary hydrogel matrix is about the same as that of the pure hydrogel matrix but much higher than that of covalently bonded nanoparticles without the support of the secondary hydrogel matrix.

The crystal hydrogels not only have all of the properties that conventional hydrogels exhibit but also have unique periodic structures. As a result, the crystal hydrogels change in volume and color in response to external stimuli including pH, electric field, salt concentration, and temperature.

Figure 10A:
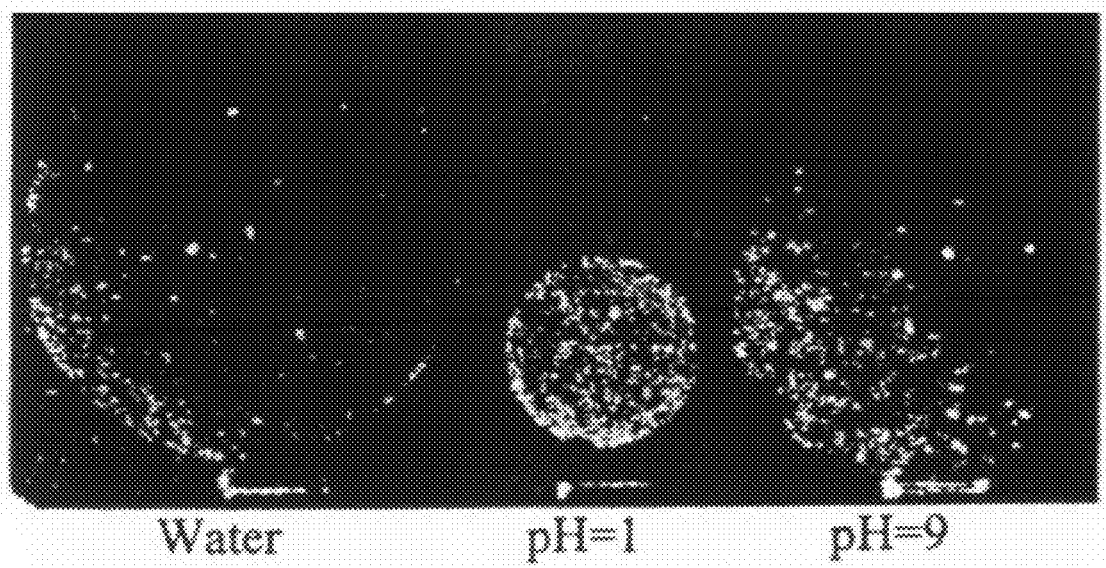
FIG. 10. pH effect on volume and color of a crystalline hydrogel consisting of bonded NIPA-HEAc nanoparticles encased in a NIPA-co-sodium acrylate hydrogel matrix. (a) The optical pictures of the sample at various pH values, (b) The change of the diameter of the sample as a function of pH.
Figure 10B:
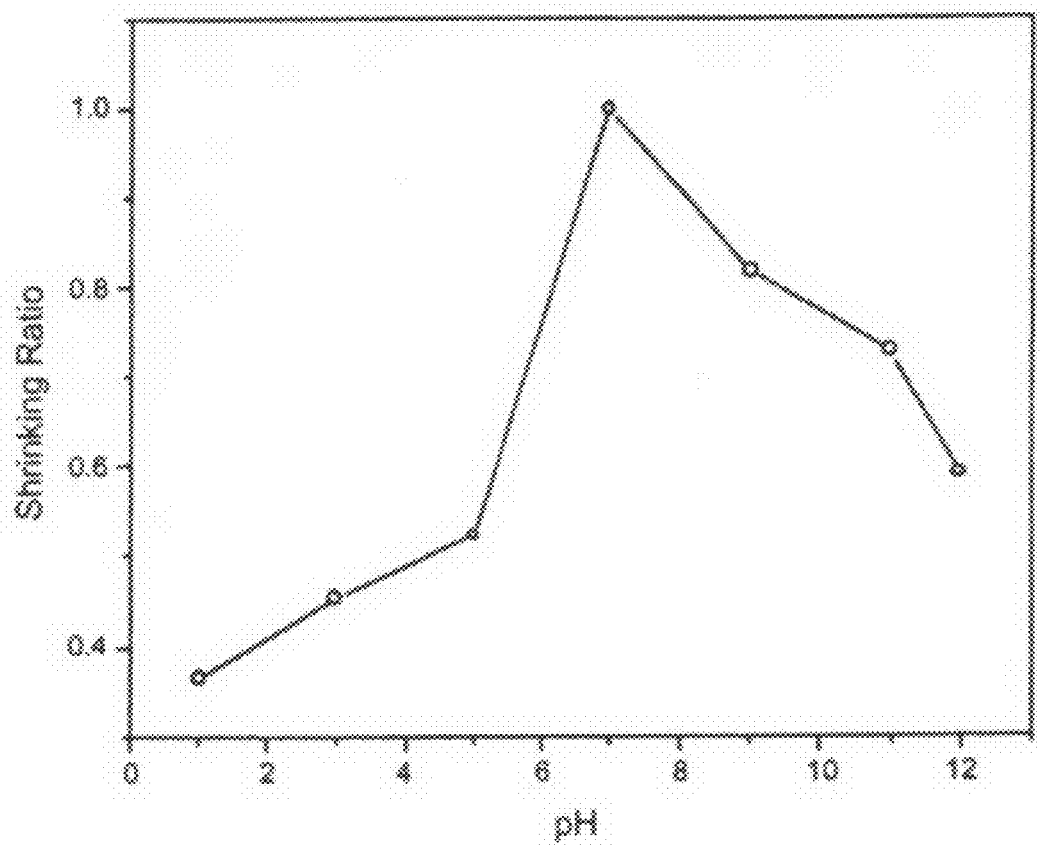

FIG. 10a shows the optical pictures of a crystal hydrogel consisting of covalently bonded, periodically stacked NIPA-HEAc nanoparticles encased within a NIPA-co-sodium acrylate matrix at various pH values. The gel swelled fully at pH=7 with large crystal grain sizes. As pH decreases or increases, the gel shrank and the crystal size becomes smaller and the crystal density increases. The detailed relationship between the gel size and the pH is shown in FIG. 10b.

Figure 11A:
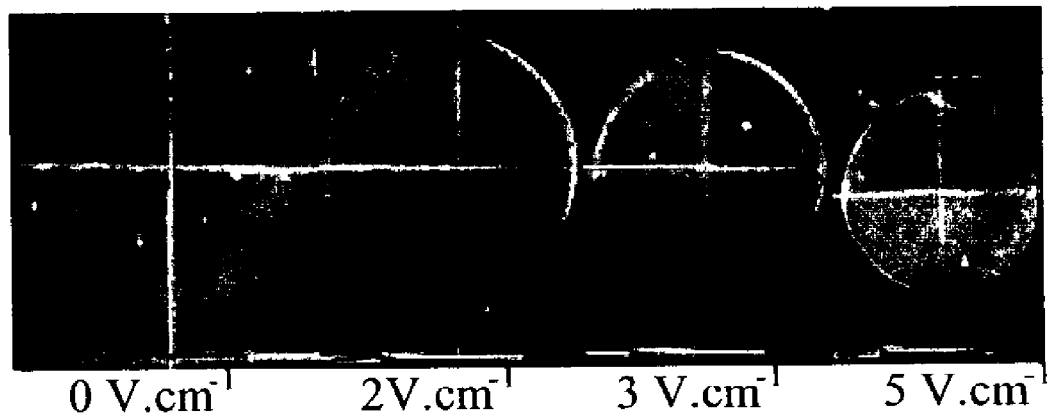
FIG. 11. Electric field effect on volume and color of a crystalline hydrogel consisting of bonded NIPA-HEAc nanoparticles encased in a NIPA-co-sodium acrylate hydrogel matrix. (a) The optical pictures of the sample at various electric fields, (b) The change of the diameter of the sample as a function of the electric field strength.
Figure 11B:
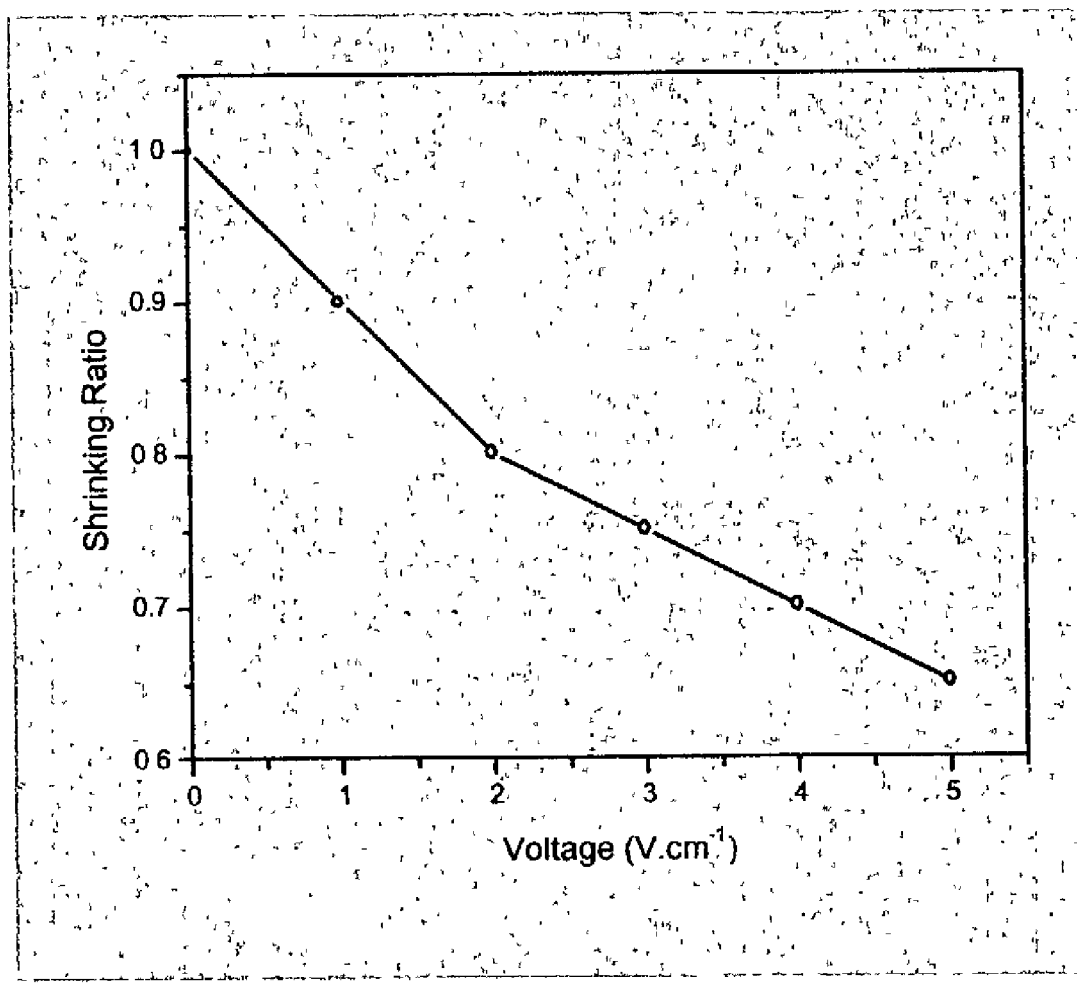

FIG. 11a shows the pictures of a hydrogel crystal under various electric fields and FIG. 11b shows the gel size as a function of the electric field. It is apparent that the gel shrinks as the electric field increases. The color of the gel also becomes more intense and shifts to blue color. The electric field causes electrolysis in the water solvent and an ionic gradient results causing a gel volume change. This effect was not observed when the electrodes were placed outside the insulating container holding the gel and its solvent while applying an electric field.

Figure 12A:
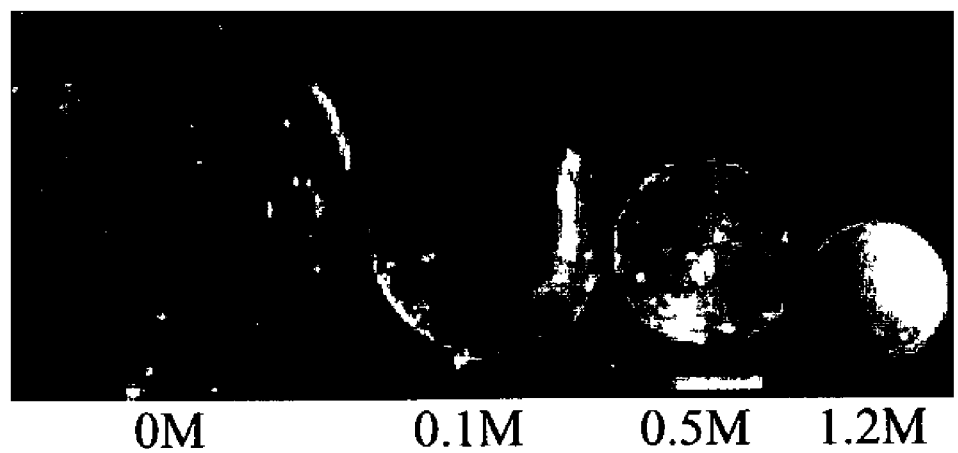
FIG. 12. Salt concentration effect on volume and color of a crystalline hydrogel consisting of bonded NIPA-HEAc nanoparticles encased in a NIPA-co-sodium acrylate hydrogel matrix. (a) The optical pictures of the sample at various salt concentrations, (b) The change of the diameter of the sample as a function of salt concentration.
Figure 12B:
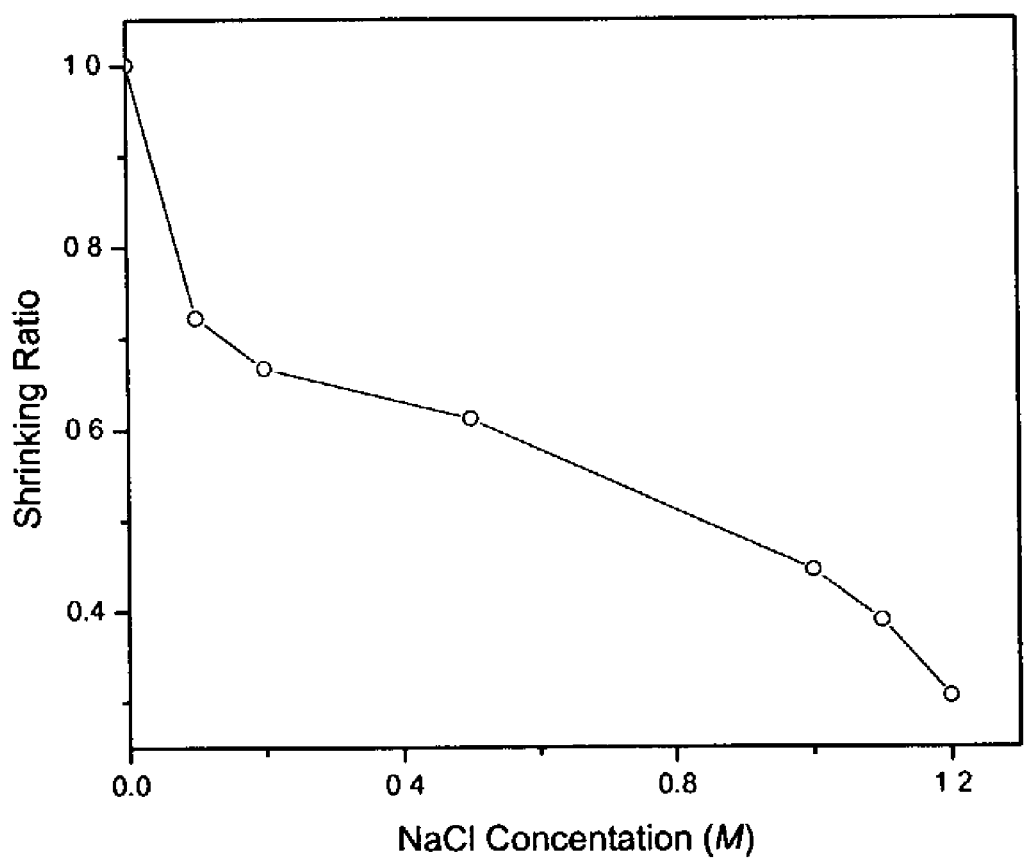

FIG. 12a shows the pictures of a hydrogel crystal under various salt concentrations and FIG. 12b shows the gel size as a function of salt concentration. It is apparent that the gel shrinks as the salt concentration increases. The color of the gel also becomes more intense and shifts to blue color upon an increase in salt concentration. The addition of increasing amounts of NaCl deteriorates the hydrogen bonding between the NIPA and water, and therefore decreases the volume phase transition temperature of the NIPA from 34° C. to room temperature.

Figure 13A:
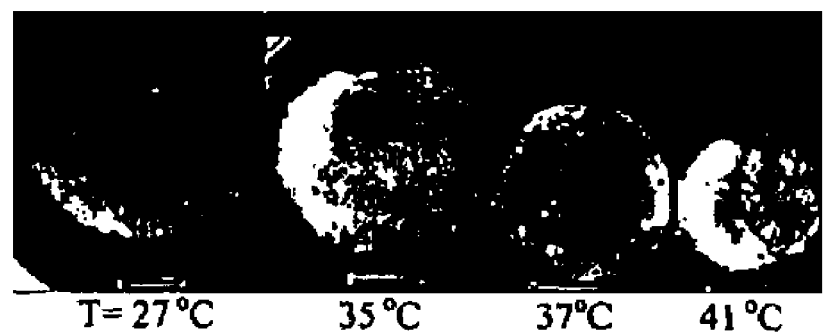
FIG. 13. Temperature effect on volume and color of a crystalline hydrogel consisting of bonded NIPA-HEAc nanoparticles encased in a NIPA-co-sodium acrylate hydrogel matrix. (*a*) The optical pictures of the sample at various temperatures, (*b*) The change of the diameter of the sample as a function of temperature.
Figure 13B:
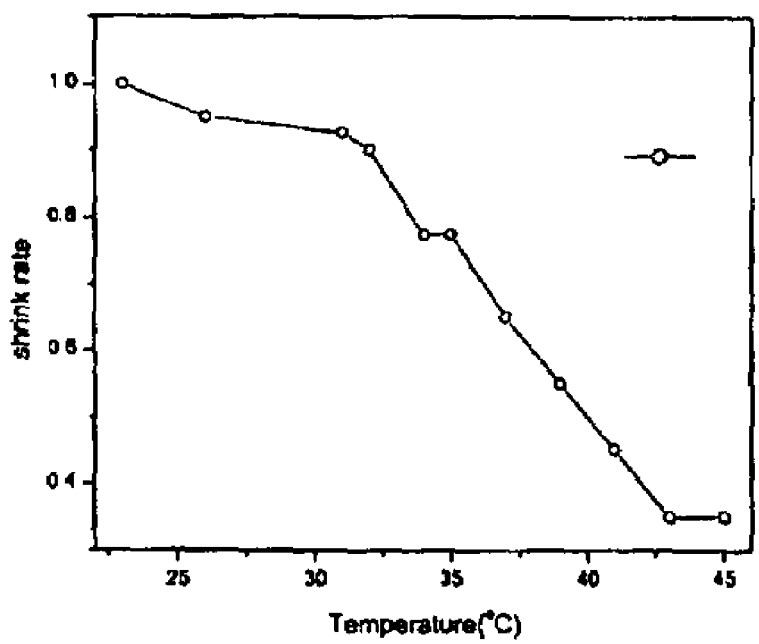

FIG. 13a shows the optical picture of a hydrogel crystal at various temperatures and FIG. 13b shows the gel size variation as a function of temperature. As the temperature increases, the gel shrinks due to intra-chain hydrophobic interaction.

The environmentally-induced color change of the crystal hydrogels can be revealed using UV-Visible spectroscopy.

Figure 14A:
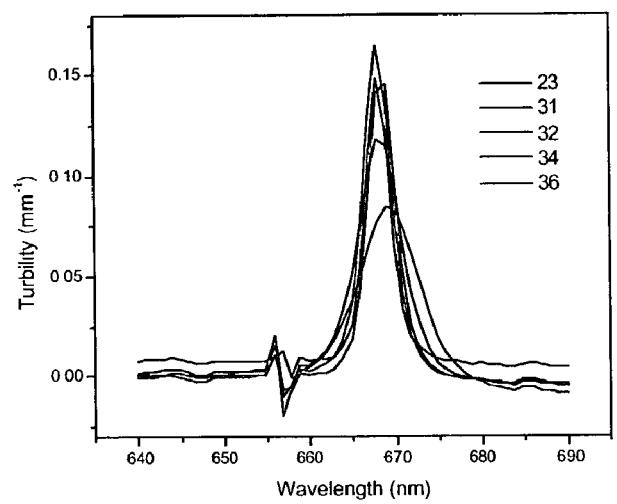
FIG. 14. Comparison of UV-Visible spectra of NIPA-HEAc nanoparticle dispersion and a crystalline hydrogel that consists of covalently linked NIPA-HEAc nanoparticles encased in a NIPA-co-acrylamide hydrogel matrix. (*a*) UV-Visible spectrum for NIPA-HEAc nanoparticles in water. The solid polymer content is 2 wt %, and (*b*) UV-Visible spectrum for the crystalline hydrogel. The peak is caused by Bragg diffraction of the crystalline particles. As the temperature changes, the peak position of hydrogel nanoparticles (*a*) does not change, but the peak position attributed to the crystalline hydrogel (*b*) does change. (*c*) Optical images of this crystal hydrogel at various temperatures.
Figure 14B:
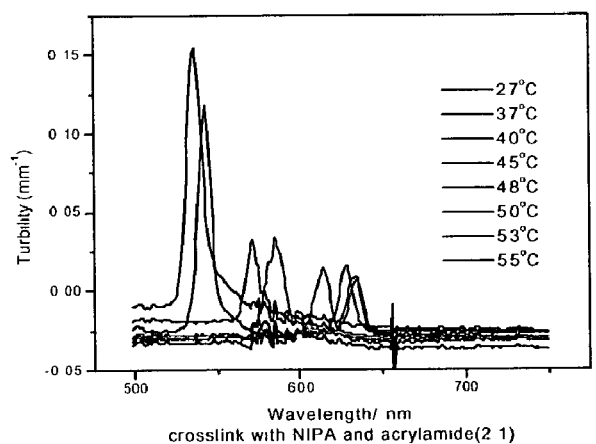
Figure 14C:
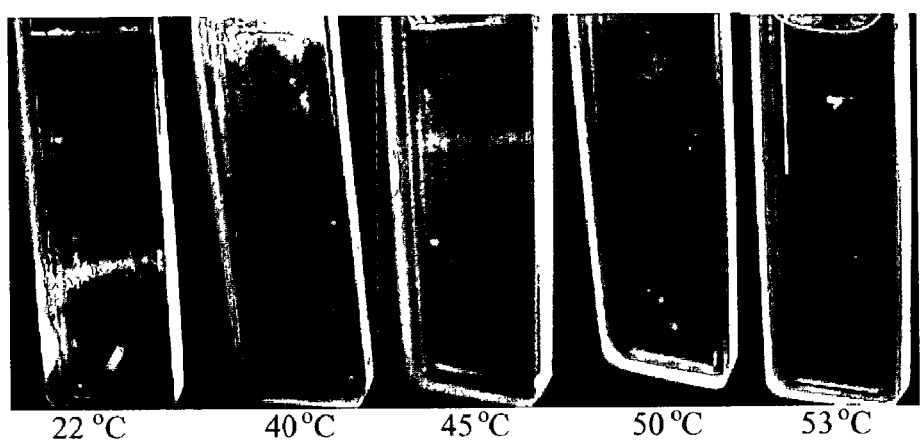

FIG. 14 shows temperature-dependent UV-visible spectra for non-bonded NIPA-HEAc nanoparticles in water and a crystal hydrogel made with covalently bonded, periodically stacked NIPA-HEAc nanoparticles encased in a NIPA-co-acrylamide matrix. As the temperature increases, the Bragg peak does not change for the nanoparticle dispersion but significantly changes for the crystal hydrogel. The color changes of the crystal hydrogel from red to blue as the temperature increases, suggesting that these unique crystalline hydrogel materials can be used as sensors.

EXAMPLE 1

Synthesis of NIPA-HEAc Nanoparticles 3.79 g NIPA monomer, 66 mg methylene-bis-acrylamide as crosslinker, 0.120 g sodium dodecyl sulphate as surfactant, and 260 mL deionized water were mixed in a reactor.

2-hydroxyethyl acrylate (HEAc) (9.5% molar ratio) used to provide functional groups was added to the pregel solution. The solution was heated to 70° C. under nitrogen for 40 min. 0.170 g of potassium persulfate dissolved in 21 mL of deionized water was added to start the polymerization reaction. The reaction was carried out at 70° C. under nitrogen atmosphere for 4 hours to ensure that all monomer was reacted. After cooling down to room temperature, the final reaction dispersion was exhaustively dialyzed in a dialysis tube for 10 days while the deionized water (conductivity of less then 1 $\mu S \cdot cm^{-1}$) outside the tube was changed twice a day. The dispersion was first evaporated at 60° C. and then dried at 120° C. The concentration of the dialyzed dispersion was calculated from the weight difference in the drying process.

TABLE 1

Compositions for synthesis of NIPA-NEAc nano-spheres with different radius

| Sample | NIPA (g) | HEAC (g) | BIS (g) | SDS (g) | Water (g) | PPS (g) | Reaction T (° C.) | Reaction t (hrs) | $R_h$ (nm) |
|---|---|---|---|---|---|---|---|---|---|
| 1 | 3.79 | 0.397 | 0.066 | 0.120 | 260 | 0.170 | 70 ± 1 | 4 | 150 |
| 2 | 3.79 | 0.397 | 0.066 | 0.100 | 260 | 0.170 | 70 ± 1 | 4 | 175 |

EXAMPLE 2

Compositions for Synthesis of NIPA-HEAc Crystal Hydrogels

The dispersion of the particles was dialyzed to remove all small molecules, and the dispersion was concentrated with ultra-centrifuging. After the concentrated dispersion was heated above the phase transition temperature, divinylsulfone (DVS) as a crosslinking agent was added to the system dropwise in order to make DVS homogeneously dispersed throughout the solution. Then, the dispersion was cooled below 25° C., and NaOH solution at pH=13.0 was added. The formation of large colloidal crystals in a very narrow concentration range (ca. 3~5 wt %), at 20° C., yields colored speckles from typical Bragg diffraction as shown in FIG. 4.

The effect of polymer concentration on formation of the crystal hydrogels is shown in Table 2. Here, the average hydrodynamic radius of the NIPA-HEAc nanoparticle spheres in water at 25° C. was 150 nm.

TABLE 2

Effect of polymer concentration on formation of the crystal hydrogels

| Sample | Conc. (wt %) | T (° C.) | $R_h$ (nm) | PH | Crystal Morphology | State |
|---|---|---|---|---|---|---|
| 1 | 2.7 | 21 | 150 | 12.0 | No crystal | Liquid |
| 2 | 2.9 | 21 | 150 | 12.0 | Large sized crystals | Liquid |
| 3 | 3.5 | 21 | 150 | 12.0 | Large sized crystals | Hydrogel |
| 4 | 3.7 | 21 | 150 | 12.0 | [62] Medium sized crystals | Hydrogel |
| 5 | 4.0 | 21 | 150 | 12.0 | Small sized crystals | Hydrogel |
| 6 | 4.2 | 21 | 150 | 12.0 | No crystals | Hydrogel |

EXAMPLE 3

Effect of NIPA-HEAc Particle Size on the Formation of Crystal Hydrogels.

The range of concentrations for forming large hydrogel crystal grains depends on the particle size. Emulsion polymerization of NIPA monomer, HEAC monomer and cross-linking agent, methylene-bis-acrylamide (BIS), was performed in water at 70° C., using different amounts of sodium dodecylsulfate (SDS, cmc of 8.3 mM in water at room temperature) as surfactant to control particle size. As shown in FIG. 5, the average hydrodynamic radii for the two red samples (left) and the two green samples (right) in water at room temperature were 175 and 150 nm, respectively. From left to right, the particle concentrations were 3.0, 3.1, 3.8, and 4.0 wt %.

EXAMPLE 4

Effect of Temperature on Formation of Crystal Hydrogels

The effect of temperature on the formation of crystal hydrogels is given by Table 3.

The crystal hydrogels are produced in one to three days within this temperature range 18-22° C.

TABLE 3

The effect of temperature on the formation of the crystal hydrogels

| Sample | T (° C.) | Concentration (wt %) | $R_h$ (nm) | pH | Crystal morphology | State |
|---|---|---|---|---|---|---|
| 1 | 17 | 3.5 | 150 | 12.0 | No | Liquid |
| 2 | 19 | 3.5 | 150 | 12.0 | Small | Hydrogel |
| 3 | 20 | 3.5 | 150 | 12.0 | Medium | Hydrogel |
| 4 | 21 | 3.5 | 150 | 12.0 | Medium | Hydrogel |
| 5 | 22 | 3.5 | 150 | 12.0 | Large | Hydrogel |
| 6 | 24 | 3.5 | 150 | 12.0 | No | Hydrogel |

EXAMPLE 5

The Effect of pH on the Formation of Crystal Hydrogels

The control of pH is as important as the control of the reaction temperature. It is found that the NaOH solution of pH>13.2 may prevent the dispersion to form a crystal structure or cause the crystal structure to be porous and cloudy. Here the pH value is given for the base solution that was dropped into the nanoparticle dispersion to make the final pH value of the dispersion about 12.

TABLE 4 shows the effect of H on the formation of the crystal hydrogels

| Sample | NaOH pH | T (° C.) | Concentration (wt %) | $R_h$ (nm) | Crystal Morphology | State |
|---|---|---|---|---|---|---|
| 1 | 12.6 | 21 | 3.0 | 175 | Large | Liquid |
| 2 | 12.8 | 21 | 3.0 | 175 | Large | Liquid |
| 3 | 13.0 | 21 | 3.0 | 175 | Large | Hydrogel |
| 4 | 13.1 | 21 | 3.0 | 175 | Large | Hydrogel |
| 5 | 13.2 | 21 | 3.0 | 175 | Medium | Hydrogel |
| 6 | 13.4 | 21 | 3.0 | 175 | No crystal | Porous gel |

EXAMPLE 6

Mechanical Stability of a Crystal Hydrogel

Figure 6:
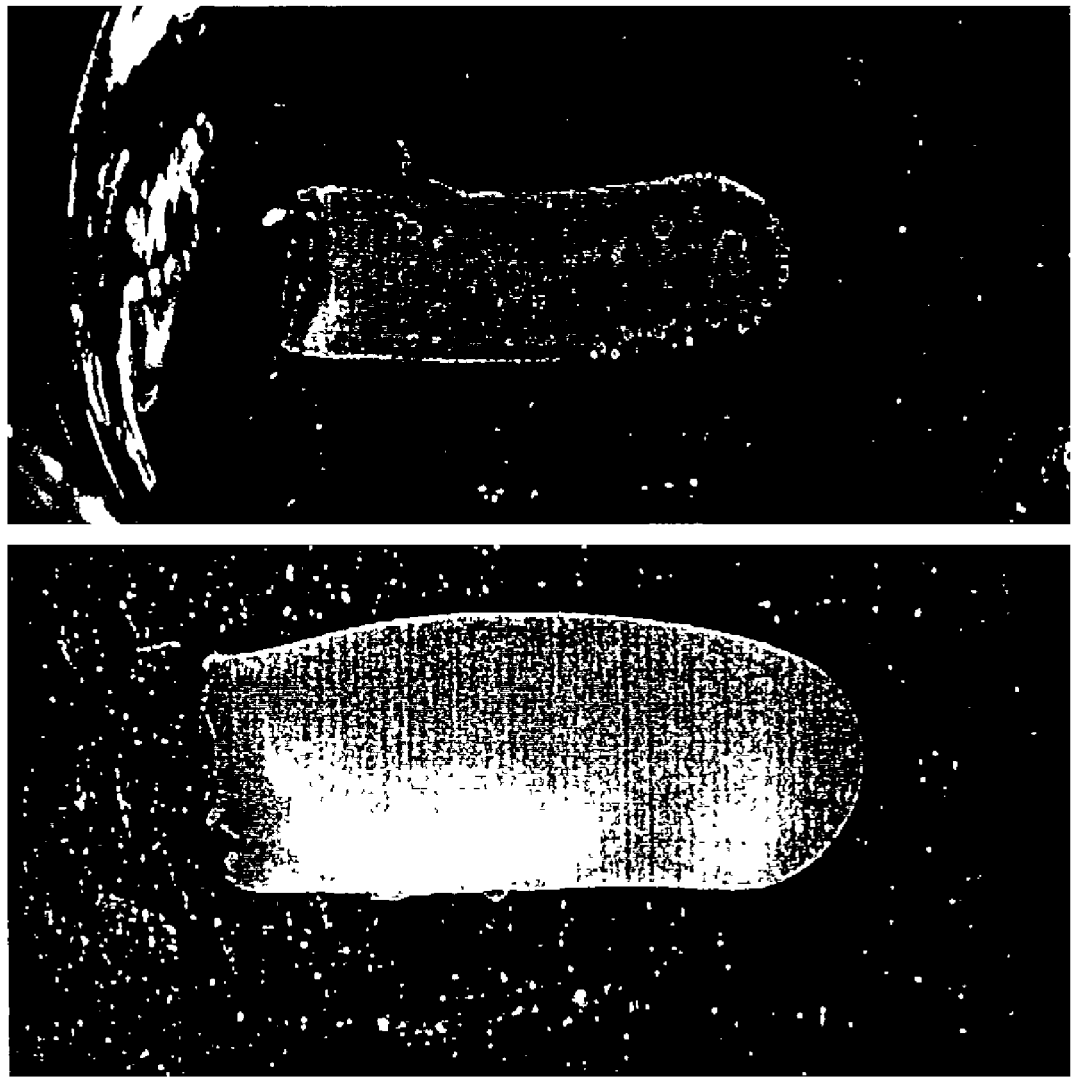
FIG. 6 shows the mechanical strength of the crystal hydrogel. The NIPA-HEAc crystal hydrogels was taken out from the glass tube and placed in a pH=2.5 solution before (top) and after (bottom) applying a weight (a transparent dish) to compress it. The bar represents 1.165 cm.

A crystal hydrogel synthesized using the methods described above was taken out from a glass tube and immersed in a pH=2.5 solution before (top) and after (bottom) applying a weight (a transparent dish) to compress it, as shown in FIG. 6. The bar represents 1.165 cm.

EXAMPLE 7

Thermal Stability of a Crystal Hydrogel

A crystal hydrogel synthesized using the methods described above in a glass tube is transparent and exhibited colored speckles at 21° C. (left) until the temperature was rasied to 50° C. (right), at which point the hydrogel lost its opalescence as shown in FIG. 7. When the sample at 50° C. was cooled back to 21° C., the colored speckles reappeared within 10 seconds.

EXAMPLE 8

Synthesis of Crystal Hydrogels Based on Poly (NIPA-co-allylamine) Nanoparticles

N-isopropylacrylamide (NIPA)-allylamine nanoparticles were synthesized using an emulsion polymerization method. 3.845 g NIPA monomer, 0.2 g (10% molar ratio) allylamine monomer, and 0.1315 g methylene-bisacrylamide as crosslinker, 0.0755 g sodium dodecyl sulfate as surfactant, and 230 ml deionized water were mixed in a reactor. The solution was heated up to 60° C. under nitrogen bubbling for about 40 min, 0.155 g potassium persulfate dissolved in 20 ml of deionized water was added to initiate the reaction. The reaction was carried out at 60° C. for 5 h. Dialysis was performed for seven days to remove the surfactant. Allylamine provides free amine functional groups on the surface of the particles for further crosslinking. The hydrodynamic radius of the nanoparticles in water was narrowly distributed with the average hydrodynamic radius at 23° C. about 140 nm. At 36° C., the microgels shrink sharply with an average radius of about 80 nm.

After using ultra-centrifuge with the speed of 40,000 rpm for 2 hrs, a condensed particle dispersion with polymer concentration of 3.5 wt % was obtained. The crosslinker glutaric dialdehyde was then added to the dispersion after the nanoparticles self-assembled into an ordered structural array. The crosslinking reaction between particles was carried out at room temperature. After 24 h, a crystal hydrogel formed that could be removed from the formation tube.

EXAMPLE 9

NIPA-allylamine Crystal Hydrogel are Responsive to Temperature and pH Changes

The crystal hydrogel obtained from Example 8 was immersed in a glass of water. At room temperature, it displayed a bright green speckles as shown in FIG. 8*a*. As the sample was heated, the color of the gel changed from green to blue gradually, and to milky white at 35° C. At the same time, the size of the gel decreased significantly. This change is fully reversible. That is, when the sample was cooled back to room temperature, it restored its color and size. The blue-color-shift is caused by the shrinkage of the particles, which made the lattice spacing smaller as the temperature increases.

Furthermore, the color of the hydrogel could be tuned by changing the pH value of the environment. FIG. 8*b* shows the photographs of the hydrogel in deionized water and in a pH=11 solution, respectively. It is evident that the color shifted from green to blue after the sample was transferred from the neutral environment to the base solution. The amine groups on the particles were partly ionized in water. However, at a higher pH value, the ionization of the basic groups was hindered, causing the shrinkage of the hydrogel. It is the decrease of the lattice spacing that leads to blue-color-shift of the hydrogel. This crystal hydrogel has a potential to be used a sensor for visual inspection of temperatures or pH values in aqueous solutions.

EXAMPLE 10

Synthesis of Crystal Hydrogels Based on NIPA-co-acrylic Acid Nanoparticles in Water The NIPA-co-AA nanoparticles were synthesized in a 500 ml flask with a nitrogen bubbling tube and a PTFE stirrer. 3.80 g N-isopropylacrylamide (NIPAAm), 0.0665 g N,N'-methylene-bis-acrylamide (BIS), 0.11 g acrylic acid (AA) and certain amount of sodium dodecyl sulfate (SDS) were added into the flask, diluted with deionized water to 250 ml solution. The flask was immersed into a water-bath at 70° C. The solution was stirred at 300 rpm for 30 minutes with a nitrogen purge to remove the oxygen inside the solution. 16.6 g Potassium persulfate (KPS) (1 wt %) was added and the reaction was carried out for 4 hours.

The NIPA-co-AA nanoparticles were then concentrated under 50° C. for two days to reach polymer concentration about 3.1 wt %. This dispersion was then put into a special cylindrical Teflon tube with numerous holes in the wall and at the bottom. The size of the holes is 0.5 mm. The NIPA-co-AA particles self-assembled into a crystalline array within 5 h as the water evaporated. Then, the tube was half-immersed into a mixture of 5 wt % 1-ethyl-3-(3-dimethylaminopropyl) carbodiimide hydrochloride (EDC or EDAC) and 5 wt % adipic acid dihydrazide (AADD). This assembly was kept at 4° C. for 24 hours and the EDC/AADD mixture was replaced by a fresh mixture of 7 wt % EDC and 7 wt % AADD. After another 24 hours, the NIPA-co-AA nanoparticles were covalently bonded into a crystalline hydrogel as shown in FIG. 9.

EXAMPLE 11

Synthesis of Crystal Hydrogels Based on NIPA-co-acrylic Acid Nanoparticles in Acetone The NIPA-co-AA nanoparticles were prepared following the procedures in Example 10.

The NIPA-co-AA particles in water were precipitated with acetone at room temperature. The precipitated particles were dried for 2 days and then re-dispersed in acetone to reach a polymer concentration of about 10 wt %. The P-NIPAAm-co-AA particles self-assembled into a crystal-line structure at room temperature. Then, epichlorohydrin (EPO) (10 wt. %) was added into the dispersion. The crosslinking reaction was carried out in the oven at 90° C. for 6 hours. The resultant crystal gel was taken out of the formation tube and immersed into acetone. Acetone was then gradually replaced with water to obtain a crystalline hydrogel.

EXAMPLE 12

Synthesis of Crystal Hydrogels by Filling the Pores Between Covalently Linked Nanoparticles with a Secondary Hydrogel Matrix The NIPA-HEAc nanoparticles were prepared following Example 1. The dispersion of the NIPA-HEAc nanoparticles was dialyzed to remove all small molecules, and was concentrated with ultra-centrifuging. This concentrated dispersion was then diluted with monomer solution that contained NIPA monomer (3 wt %), a co-monomer (0.03 wt %) of sodium acrylate (NaAc), a photo-sensitive initiator of 2,2-diethoxyacetophenone at 1.0 wt % NIPA content, N,N'-methylenebisacrylamide at 5.0 wt % NIPA content as crosslinker. The particle concentration reaches about 2.0wt % and the monomers of the NIPA reaches 3.0 wt % in the final dispersion. The dispersion was thoroughly bubbled with nitrogen gas to remove oxygen. This dispersion was heated to 40° C., divinylsulfone (DVS) as a crosslinking agent was added to the system dropwise in order to make DVS homogeneously dispersed throughout the solution. Then, the dispersion was cooled below 25° C., and NaOH solution was added to make a pH=12 dispersion. The formation of colloidal crystals provided colored speckles from typical Bragg diffraction. The nanoparticles were then crosslinked using DVS to stabilize the crystal structure and allowed to sit for 24 hours. Then, a UV lamp was used to initiate polymerization of NIPA monomers to encase the crystal hydrogel. The sample was kept in a nitrogen environment for 24 hr to complete gelation.

The shear modulus of the crystal hydrogel incased within a secondary hydrogel matrix is about the same as that of the pure hydrogel matrix of about $1 \times 10^4$ dyn/cm$^2$ but much higher than that of covalently bonded nanoparticles without the support of the secondary hydrogel matrix.

EXAMPLE 13

The Effect of pH on Crystal Hydrogels

The resultant hydrogel crystal from Example 12 consists of covalently bonded, periodically stacked NIPA-HEAc nanoparticles within a NIPA-co-sodium acrylate matrix. The NIPA-HEAc nanoparticles provide periodical structures for Bragg diffraction and the NIPA-co-sodium acrylate provided a matrix to enhance the strength and introduce additional environmentally responsive properties.

FIG. 10a shows the optical pictures of this hydrogel crystal as a function of pH. The gel swelled fully at pH=7 with a large crystal grain size. As pH decreases or increases, the gel shrinks and the crystal size becomes smaller and the crystal density increases. The detailed relationship between the gel size and the pH is shown in FIG. 10b. At low pH, protons are attached to COO— by hydrogen bonding so that the osmotic pressure due to COO— ions is significantly reduced. On the other hand, at higher pH values, all of the free COO— was bonded to Na+ ions, resulting in shrinkage of the gel.

EXAMPLE 14

The Effect of Electric Field on Volume and Color of Crystal Hydrogels

The crystal hydrogels were produced using the methods and chemical compositions listed in Example 10. They consisted of covalently bonded, periodically stacked NIPA-HEAc nanoparticles within a NIPA-co-sodium acrylate hydrogel matrix. FIG. 11a shows the pictures of the hydrogels crystal under various electric fields and FIG. 11b shows the gel size as a function of the electric field. It is apparent that the gel shrinks as the electric field increases. The color of gel also becomes more intense and shifts to blue color. The electric field caused electrolysis in the water solvent and an ionic gradient that causes a gel volume change. This effect was not observed when the electrodes were placed outside the insulating container holding the gel and its solvent while applying an electric field.

EXAMPLE 15

The Effect of Salt Concentration on Volume and Color of the Crystal Hydrogels The experimental samples were produced using the methods and chemical compositions listed in Example 10. These hydrogel crystals consisted of covalently bonded, periodically stacked NIPA-HEAc nanoparticles within a NIPA-co-sodium acrylate hydrogel matrix.

FIG. 12a shows the pictures of the hydrogels crystal under various salt concentrations and FIG. 13b shows the gel size as a function of salt concentration. It is apparent that the gel shrinks as the salt concentration increases. The color of gel also becomes more intense and shifts to blue color upon the increase of salt concentration. The addition of increasing amounts of NaCl disrupts the hydrogen bonding between the NIPA and water, and therefore decreases the volume phase transition temperature of the NIPA from 34° C. to room temperature.

EXAMPLE 16

The Effect of Temperature on Volume and Color of the Crystal Hydrogels

The crystal hydrogels were prepared as outlined in Example 10. FIG. 13a shows the optical pictures of the hydrogel crystal at various temperatures and FIG. 13b shows the gel size as a function of temperature. As the temperature increases, the gel shrinks due to intra-chain hydrophobic interaction.

EXAMPLE 17

UV-Visible Spectroscopy of the Crystal Hydrogels

The same method and chemical compositions as outlined in Example 10 were used except the sodium acrylate monomer was replaced with acrylamide. The final composition of NIPA to AAM molar ratio is 2:1. The resultant hydrogel crystal consists of covalently bonded, periodically stacked NIPA-HEAc nanoparticles within a NIPA-co-acrylamide hydrogel matrix. FIG. 14 shows temperature-dependent UV-visible spectra for non-bonded NIPA-HEAc nanoparticles in water and a crystal hydrogel made with covalently bonded, periodically stacked NIPA-HEAc nanoparticles encased in a NIPA-co-acrylamide matrix. As the temperature increases, the Bragg peak does not change for the nanoparticle dispersion but significantly changes for the crystal hydrogel.

Those skilled in the art will recognize that, while specific embodiments and examples have been described, various modifications and changes may be made without departing from the scope and spirit of the invention.

The following U.S. patents, foreign patents and applications and other references are incorporated by referenced herein.

| U.S. PATENTS AND PATENT APPLICATIONS | | | |
| --- | --- | --- | --- |
| 60/311,036 | July, 2001 | Hu, et al | |
| Re35068 | October, 1995 | Tanaka et al. | 523/300. |
| 4,732,930 | March, 1988 | Tanaka et al. | 524/742. |
| 5,100,933 | March, 1992 | Tanaka et al. | 523/300. |
| 5,183,879 | February, 1993 | Yuasa et al. | 528/503. |
| 5,403,893 | April, 1995 | Tanaka et al. | 525/218. |
| 5,532,006 | July, 1996 | Lauterber et al. | 424/9.322 |
| 5,580,929 | December, 1996 | Tanaka et al. | 525/218. |
| 6,030,442 | February, 2000 | Kabra, et al. | 536/84 |
| 4,912,032 | March, 1990 | Hoffman, et al. | 435/7.1 |
| 6,194,073 | February, 2001 | Li, et al. | 428/420 |
| 5,976,648 | November, 1999 | Li, et al. | 428/34. |
| 5,062,841 | November, 1991 | Siegel | 604/891.1 |
| 5,654,006 | August, 1997 | Fernandez, et al. | 424/489 |
| 6,030,442 | February, 2000 | Kabra, et al. | 106/162.8 |
| 4,555,344 | November, 1985 | Cussler | |
| 6,187,599 | February, 2001 | Asher, et al. | 436/531 |
| 6,165,389 | December, 2000 | Asher, et al. | 252/582 |
| 6,014246 | January 2000 | Asher, et al. | 359/288 |
| FOREIGN PATENTS | | | |
| 0 365 011 A2 | April, 1990 | | EP |
| 2-155952 | June, 1990 | | JP |
| 3-701 | January, 1991 | | JP |
| 7-82325 | March, 1995 | | JP |
| 7-292040 | November, 1995 | | JP |
| WO 91/05816 A1 | May, 1991 | | WO |
| WO 92/02005 A2 | February, 1992 | | WO |
| WO 95/31498 A1 | November, 1995 | | WO |

OTHER REFERENCES

Peppas, N. A., Hydrogels in Medicine and Pharmacy, (CRC Press, Boca Raton, Fla., 1987).

Tanaka, T., "Collapse of gels and the critical endpoint," Phys. Rev. Lett. 40, 820-823 (1978).

Osada, Y., et al., "Intelligent gels," Scie. Ame. 268, 82-87 (1993).

Siegel, R. A., et al., "pH-dependent equilibrium swelling properties of hydrophobic polyelectrolyte copolymer gels," Macromol. 21, 3254-3259 (1988).

Chen, et al., "Graft copolymer compositions that exhibit temperature-induced transitions over a wide range of pH," Nature 373, 49 (1995).

Weissman, J. M., et al., "Thermally switchable periodicities and diffraction from mesoscopically ordered materials," Science 274, 959-960 (1996).

Holtz, J. H., et al. "Polymerized colloidal crystal hydrogel films as intelligent chemical sensing materials," Nature 389, 829-832 (1997).

Hu, Z, et al., "Synthesis and application of modulated polymer gels," Science 269, 525-527 (1995).

Hu, Z, et al., "Polymer gel nanoparticle networks," Adv. Materials 12, 1173 (2000).

Lu, et al., "Synthesis and light scattering study of hydroxypropyl cellulose microgel," Macromolecules 33, 8698-8702 (2000).

Pelton, R. H., et al., "Preparation of Aqueous Latices with N-Isopropylacrylamide." Colloids and Surfaces 20, 247-256 (1986).

Hirotsu, S., et al., "Volume-phase transitions of ionized N-isopropylacrylamide gels," J. Chem. Phys. 87, 1392-1395 (1987).

Clark, N. A. et al. "Single colloidal crystals," Nature 281, 57-60 (1979).

Pusey, P. N., et al. "Phase behavior of concentrated suspensions of nearly hard colloidal spheres," *Nature* 320, 340 (1986).

Senff, H., et al. "Temperature sensitive microgel suspensions: colloidal phase behavior and rheology of soft spheres," *J. Chem. Phys.* 111, 1705-1711 (1999).

Sanders, J. V., Nature 204, 1151 (1964).

Krieger, I. M., J. "Diffraction of light by arrays of colloidal spheres," *J. Amer. Chem. Soc.* 90, 3115-3120 (1968).

What is claimed is:

1. A crystal hydrogel material comprising covalently bonded, periodically stacked, monodispersed gel nanoparticles dispersed throughout a liquid medium in a crystalline lattice, wherein neighboring gel nanoparticles are covalently linked using small molecular crosslinkers, and wherein the crystal hydrogel material demonstrates visible opalescence contributed by Bragg diffraction from the crystalline lattice of periodically stacked nanoparticles.

2. The crystal hydrogel material of claim 1 where the medium is water.

3. The crystal hydrogel material of claim 1, wherein covalent bonding contributes to mechanical, dimensional, and thermal stability of nanosphere assemblies, while periodic structure of the gel nanoparticles diffracts light to cause a range of opalescence.

4. The crystal hydrogel material of claim 1 defined further as displaying an iridescent color with good transparency and no sedimentation in the absence of an index-matching or a density-matching fluid.

5. The crystal hydrogel material of claim 1 defined further as containing at least 75% water by weight.

6. The crystal hydrogel material of claim 1 defined further as containing about 90% water by weight.

7. The crystal hydrogel material of claim 1 defined further as containing at least 97% water by weight.

8. The crystal hydrogel material of claim 1 defined further as changing in color and volume in response to environmental conditions.

9. The material of claim 8 where the environmental conditions are pH, temperature, electric current, ionic strength or type of solvent.

10. The crystal hydrogel material of claim 1 defined further as exhibiting different colors when different particle sizes, particle concentrations, chemical composition of the particles or reaction temperatures are used to produce the particles.

11. The crystal hydrogel material of claim 1 in which crystalline grain size changes as a function of particle size, particle concentration, particle stacking or particle chemical composition.

12. The crystal hydrogel material of claim 1 where optimum conditions in which to form said crystal hydrogel are dependent upon specific temperature and pH ranges.

13. The crystal hydrogel material of claim 1 comprising gel nanoparticles contain N-isopropylacrylamide and derivatives thereof.

14. The crystal hydrogel material of claim 1 comprising nanoparticles in a particle size range of 1-1000 nanometers in diameter.

15. The crystal hydrogel material of claim 1 comprising nanoparticles in particle size range of 1-500 nanometers diameter.

16. The crystal hydrogel material of claim 1 comprising nanoparticles in a particle size range of 20-5 00 nanometers in diameter.

17. The crystal hydrogel material of claim 1 comprising nanoparticles that are internally crosslinked using crosslinking compounds.

18. The crystal hydrogel material of claim 1 whose particles are bonded through functional groups on the surfaces of neighboring particles using crosslinking compounds.

19. The crystal hydrogel material of claim 1 comprising covalent linkages between nanoparticles that provide a thermal and dimensional stable crystal structure.

20. The crystal hydrogel material of claim 17 wherein the crosslinking compounds comprise methylene-bis-acrylamide.

21. The crystal hydrogel material of claim 18 wherein the crosslinking compounds are selected from the group consisting of divinylsulfone related analogs, glutaric dialdehyde or related analogs, 1-ethyl-3-(3-dimethylaminopropyl)carbodiimide hydrochloride (EDC), adipic acid dihydrazide and other related analogs.

22. The crystal hydrogel material of claim 1 encased within a secondary polymer matrix.

23. The crystal hydrogel material of claim 22 where the secondary polymer matrix are selected from the group consisting of N-isopropylacrylamide, hydroxypropylcellulose, polyvinyl alcohol, polypropylene oxide, polyethylene oxide, polyethylene oxide/polypropylene oxide copolymers, and another known hydrogel polymer.

24. The crystal hydrogel material of claim 1 or 22 whose volume and color change reversibly in response to an external stimulus.

25. The crystal hydrogel material of claim 24 where the stimulus is pH, electric field, ionic strength or temperature.

26. The crystal hydrogel material of claims 1 or 22 that, when viewed at different angles and under various lighting conditions, exhibits multiple prism-like light diffraction patterns.

27. The crystal hydrogel material of claim 1 or 22 whose optical properties change reversibly as either pH, temperature, ionic strength or electric current of the surrounding environment changes.

* * * * *